United States Patent [19]

Bradstock et al.

[11] Patent Number: 5,179,019
[45] Date of Patent: Jan. 12, 1993

[54] THERAPEUTIC MURINE MONOCLONAL ANTIBODY

[75] Inventors: Kenneth F. Bradstock, Drummoyne; Michael K. Atkinson, Palm Beach; Anthony J. Henniker, Wahroonga, all of Australia

[73] Assignee: Biomedical Systems Limited, Australia

[21] Appl. No.: 582,882

[22] PCT Filed: Mar. 31, 1989

[86] PCT No.: PCT/AU89/00139
§ 371 Date: Nov. 21, 1990
§ 102(e) Date: Nov. 21, 1990

[87] PCT Pub. No.: WO89/09234
PCT Pub. Date: Oct. 5, 1989

[30] Foreign Application Priority Data

Mar. 31, 1988 [AU] Australia .................. PI7546

[51] Int. Cl.$^5$ .............. C12N 5/20; C07K 15/28; C12P 21/08
[52] U.S. Cl. ............... 435/240.27; 435/240.26; 530/388.1; 530/388.2; 530/388.7; 530/388.73; 530/388.75; 530/388.85; 935/103

[58] Field of Search ............... 530/387, 388.1, 388.2, 530/388.7, 388.73, 388.75, 388.85; 435/240.27, 240.26; 935/103

[56] References Cited

FOREIGN PATENT DOCUMENTS 8048887 5/1989 Australia .
8900169 1/1989 PCT Int'l Appl. .

OTHER PUBLICATIONS

LeBien et al., The Journal of Immunology, vol. 125, No. 5, pp. 2208-2214 (1980).

Primary Examiner—Y. Christina Chan
Attorney, Agent, or Firm—Christie, Parker & Hale

[57] ABSTRACT

The present invention relates to a monoclonal antibody which is broadly reactive with all normal human peripheral blood mononuclear cells and granulocyte, and to the hybridoma cell line which produces this monoclonal antibody. This monoclonal antibody is designated WM-65 and the hybridoma cell line is designated F56-1D5 (ECACC 89033001). This monoclonal antibody reacts with a previously unrecognized human leucocyte surface membrane antigen. The relative molecular mass of the antigen recognized by WM-65 is approximately 40-50 Kilodaltons.

2 Claims, 4 Drawing Sheets

Fig. 3

THERAPEUTIC MURINE MONOCLONAL ANTIBODY

FIELD OF THE INVENTION

The present invention relates to a new hybridoma cell line and to the monoclonal antibody produced by this hybridoma cell line This monoclonal antibody reacts with a novel human leucocyte surface membrane antigen with wide distribution within the haemopoietic system.

BACKGROUND OF THE INVENTION

Since it was shown by Kohler & Milstein (Nature Vol. 256, 495–497, 1975) that it was possible to fuse mouse myeloma cells with spleen cells from immunized mice and thereby product a continuous cell line which produces a homogeneous (monoclonal) antibody, extensive attention has been focused on the production of these hybrid cell lines (hybridomas) and the monoclonal antibodies (Mabs) produced.

The development of hybridoma technology has led to a dramatically improved understanding of the antigenic molecules on the surface of human leucocytes, and over the past decade, many murine monoclonal antibodies reacting with haemopoietic cell surface antigens have been described. Following the three International Workshops on Human Leucocyte Differentiation Antigen, the majority of these antibodies have been grouped into Clusters of Differentiation (CD), and have been shown to react with restricted differentiation-lineage or maturation stage membrane antigens on lymphoid or bone marrow-derived cells (Interim Report of the 3rd Workshop Nomenclature Committee (1987) in A.J. McMichael, Ed. Leucocyte Typing III. White cell differentiation antigen. Oxford University Press, PP 949–950).

A few antibodies have been shown to have broader haemopoietic cellular reactivity. The best characterised are the antibodies fitting into CD 45 or CD 45R, which identify a family of antigens with molecular weights around 200 Kilodaltons expressed on virtually all human leucocytes (Pizzolo et al., Cancer, 1980, 46, 2640–2647; Dalchau et al., 1980, European Journal of Immunology, 10, 737–744). Other unclustered Mabs with non-lineage reactivity include PHM-1, CAMPATH-1, HuLyM3, which appear to identify separate and unique antigens (Becker et al., 1981, Pathology, 13, 669–680; Hale et al., 1983, Blood, 62, 873–882; Vaughan et al., Transplantation, 36, 446–450).

SUMMARY OF THE INVENTION

In a first aspect, the present invention consists in a mouse monoclonal antibody of class IgG$_1$ produced by a hybridoma formed by a fusion of cells from a mouse myeloma line and spleen cells from a mouse previously immunized with the T cell line HSB-2 and T-CLL cells, the monoclonal antibody being characterised in that it reacts with a leucocyte surface membrane antigen of a relative molecular weight of approximately 40–50 Kilodaltons which is expressed on over 90% of normal human peripheral blood mononuclear cells and granulocytes, but not on normal platelets or erythrocytes.

It is preferred that the monoclonal antibody is further characterised in that it:
a) reacts with approximately 90% of normal human thymocytes;
b) reacts with human B cell leukemia lines RAji, Daudi and Bristol 8;
c) reacts with human T cell leukemia lines T-All, MOLT-4, CEM, HSBO2;
d) reacts with the Myeloid cell line K562;
e) reacts with pre-B cell lines NALM-6, Reh, KM3;
f) reacts with approximately 95% of mitogen activated human lymphocytes;
g) is unreactive with the cell lines IPMI-8402, U937, Rc2a, and H160; and
h) is unreactive with platelets or erythrocytes.

In a second aspect the present invention consists in an IgG$_1$ monoclonal antibody-producing hybridoma cell line formed by fusion of cells from a mouse myeloma line and spleen cells from a mouse previously immunized with the T cell line HSB-2 and T-CLL cells, the monoclonal antibody produced being characterised in that it reacts with a leucocyte surface membrane antigen of a relative molecular weight of approximately 40–50 Kilodaltons which is expressed on over 90% of normal human peripheral blood mononuclear cells and granulocytes, but not on platelets or erythrocytes.

It is preferred that the monoclonal antibody produced is further characterised in that it:
a) reacts with approximately 90% of normal human thymocytes;
b) reacts with human B cell leukemia lines RAji, Daudi and Bristol.8;
c) reacts with human T cell leukemia lines T-All, MOLT-4, CEM, HSB.2;
d) reacts with the Myeloid cell line K562;
e) reacts with pre-B cell lines NALM-6, Reh, KM3;
f) reacts with approximately 95% of mitogen activated human lymphocytes;
g) is unreactive with the cell lines IPMI-8402, U937, Rc2a, and H160; and
h) is unreactive with platelets or erythrocytes.

The monoclonal antibody of the first aspect of the present invention has been designated WM-65, and the hybridoma cell line of the second aspect of the present invention has been designated F56-1D5. This hybridoma cell line was deposited with the European Collection of Animal Cell Cultures (ECACC), PHLS Centre for Applied Microbiology and Research, Porton Down, Salisbury, Wilts., United Kingdom on Mar. 30, 1989 and was accorded accession number 89033001.

The disclosure of this deposit is herein incorporated by way of cross-reference. The monoclonal antibody of the first aspect of the present invention will hereafter be referred to as WM-65 and the hybridoma cell line of the second aspect of the present invention will hereafter be referred to as F56-1D5.

DETAILED DESCRIPTION OF THE INVENTION

The hybridoma cell line F56-1D5 was produced using the technique described in detail below, and the monoclonal antibody WM-65 produced by this hybridoma cell line was tested using the techniques described below.

BRIEF DESCRIPTION OF DRAWINGS

In order that the nature of the present invention may be more clearly understood preferred forms thereof will be described with reference to the accompanying drawings in which:

FIG. 1 shows the flow cytometric evaluation of WM-65 reactivity with normal peripheral blood mononuclear cells. Log green fluorescence is indicated on the horizontal scale and log red fluorescence on the vertical scale. FIG. 1B), CD-3 Mab (OKT-3-PE; FIG. 1C), or CD-11c Mab (Leu M5.PE; FIG. 1D) directly conjugated with Phycoerythrin. The results illustrate that virtually all CD-19+, CD-3+, and CD-11c+ cells are labelled by WM-65 (indicated in quadrant II in each FIG.).

FIG. 2 shows representative immunofluorescence reactivity patterns of WM-65 with cases of AML(FIG. 2A), and common ALL(FIG. 2B). Staining was evaluated in a flow cytometer with log fluorescence intensity displayed on the horizontal axis and cell numbers of the vertical axis. Heavy tracing indicates the fluorescence $IgG_1$ negative control MAB, and the light tracing is WM-65 staining

MATERIALS AND METHODS

Immunization and Hybridoma Production

An 8 week old female BALB/c mouse was injected intraperitoneally with $10^7$ cells of the human T-leukemia cell line HSB-2. Five days later $5 \times 10^6$ peripheral blood leucocytes from a patient with a T cell form of chronic lymphocytic leukemia (T-CLL) were injected intraperitoneally. Twenty days later a further $8 \times 10^6$ T-CLL lines were injected Three days later the animal was sacrificed and the spleen removed. Splenic lymphocytes were fused with the mouse myeloma cell line P3-NS1-Ag3, using a modification of the method described by Kohler and Milstein (Nature, 1975, 26, 495-497; and Fazekas de St. Groth et al, 1980, Journal of Immunological Methods, 35, 1-21). Following fusion, cells were plated out in DULBECCO'S MINIMAL ESSENTIAL MEDIUM (DMEM) a tissue culture medium containing foetal calf serum (FCS: Flow Laboratories), L-glutamine, sodium pyruvate, antibiotics and hypoxanthine-aminopterin-thymidine (HAT; Flow Labs.), into 96 well microtitre plates (Linbro).

Culture supernatants from wells containing hybridomas were tested for reactivity on peripheral blood mononuclear cells. One hybridoma, F56-1D5, was selected, and cloned three times by the limiting dilution method Monoclonal antibody was produced by injecting $10^7$ hybridoma cells intraperitoneally into pristane-primed mice, and collecting ascitic fluid.

Preparation of Cells for Antibody Characterization

Mononuclear cells were isolated from heparinized peripheral blood obtained from healthy volunteers by centrifugation on FICOLL-HYPAQUE (Pharmacia), a centrifugation medium, while granulocytes were prepared from the same source using MONO-POLY (Pharmacia), a centrifugation medium. Tonsil and thymic lymphocytes were obtained from fresh surgical samples. The tissue was cut and teased in medium to produce a single cell suspension. The cells were washed and tested immediately, or cryopreserved until required.

Leukaemic cells were obtained from heparinized bone marrow or peripheral blood diagnostic samples, and separated on FICOLL-HYPAQUE. Cells were either used fresh or cryopreserved until required. Leukaemic cell lines were grown in RPMI 1640 (Flow Labs.) containing FCS, L-glutamine and antibiotics.

Immunofluorescence Staining and Flow Cytometry

Peripheral blood leucocytes were prepared for immunofluorescent staining as described previously (Bradstock et al, 1985, Pathology, 17, 392-399). Briefly, $1-2 \times 10^6$ cells were reacted at 20° C. with a saturating concentration of Mab for 10 minutes, then washed in phosphate buffered saline containing 0.1% sodium azide (PBSA), followed by incubation with sheep anti-mouse antiserum conjugated to fluorescein isothiocyanate (SAM-FITC; Silenus) for a further 10 minutes at room temperature. For characterization of subsets of normal peripheral blood mononuclear cells, two colour direct immunofluorescence was used. Leucocytes were stained with WM-65 directly conjugated to FITC, and with Mabs to CD-3 (OKT-3 PE), CD-11c (Leu M5-PE), or CD-19 (B4 PE) all directly conjugated with Phycoerythrin. After completion of immunofluorescence staining, cells were then washed again, and reactivity determined using a FACS 440 cytometer (Becton Dickinson, Calif.). An isotype-matched Mab unreactive with human cells was used as a negative control.

Complement Mediated Cytoxicity

The lytic ability of the Mab was tested in a complement-mediated cytoxicity assay as previously described. Briefly, $10^6$ peripheral blood mononuclear cells were incubated with a saturating concentration of Mab for 15 minutes at room temperature. This was followed by the addition of an equal volume of rabbit serum (Pelfreez), and further incubation at 37° C. for 45 minutes. A Mab (W6-32; Sera Labs.) reactive with human Class 1 MHC antigens was used as a positive control Cell viability was determined by Trypan blue exclusion using an inverted microscope.

Reactivity with Bone Marrow Progenitor Cells

Normal bone marrow was obtained with the informed consent of normal volunteers undergoing harvest for allogeneic bone marrow transplantation. Mononuclear cells were separated on FICOLL-HYPAQUE, washed, then reacted with a saturating solution of Mab or with the appropriate negative control for 10 minutes at 20° C. After washing with PBS the cells were incubated with SAM-FITC, for a further 10 minutes at 20° C., washed again, and then sorted into fluorescence positive and negative populations in a FACS440 cell sorter. Leucocytes from each population were plated at $1 \times 10^5$ viable cells in quadruplicate in 0.3% agar containing 25% FCS in 35 mm Petri dishes, with a 0.5% agar underlayer containing $1 \times 10^6$ irradiated normal peripheral blood mononuclear cells as a feeder layer. Plates were incubated in 5% $CO_2$ in air at 37° C., and examined at day 12 using an inverted microscope. Colonies were scored as groups of more than 40 cells.

Immunoprecipitation and Electrophoresis

Antigenic molecular weight determination was performed as previously described (Bradstock et al, 1985, Pathology, 17, 392–399). Peripheral blood mononuclear cells were surface-labelled with $^{125}$I using the lactoperoxidase method Cells were disrupted using TRITON-X 100, a detergents and centrifuged to remove cytoskeletal material The radiolabelled lysate was precleared overnight using PANSORBIN (Pharmacia), an absorption medium. The cell lysate was reacted with Mab for 2 hours at 4° C. followed by a further 30 minutes incubation with goat antimouse IgG (Cappell). The complex was absorbed onto PABNSORBIN and resuspended in non-reducing electrophoresis buffer. Samples were reduced by the addition of 15 ul mercaptoethanol Samples, together with molecular weight markers (Biorad), were run on a 5–15% gradient polyacrylamide gel overnight. The gels were stained with Coomassie Brilliant Blue, dried and autoradiographs performed using HYPERFILM(Amersham), an X-ray film at −70° C.

Tissue Section Staining

Fresh tissue biopsies were snap frozen in isopentane and stored in liquid nitrogen Cryostat sections 6 to 8 microns thick were air dried onto poly-L-Lysine (Sigma) treated slides, fixed in acetone at −10° C. for 5 minutes, and washed with 3% hydrogen peroxide in 0.05 M Tris-HCl/phosphate buffered saline, pH 7.6, for 5 minutes to block endogenous peroxidase. Tissue sections were then washed in Tris-buffered saline for 15 minutes. Prior to immunohistochemical staining, sections were incubated with diluted normal horse serum (Vectastain ABC kit, No. PK4002) for 5 minutes to reduce non-specific binding of the secondary antibody. Mab (or the isotype-matched negative control) in the form of 1:10 dilution of culture supernatant was then added to the sections, and incubated for one hour in a humidified chamber on a platform rocker. The slides were washed in Tris-PBS and incubated with an appropriate dilution of biotinylated horse anti-mouse antibody (Vectastain) for 20 minutes. After further washing in Tris-PBS, sections were incubated for 30 minutes with avidin-horseradish peroxidase complex (Vectastain), washed again, then developed for 4 minutes in DAB solution (0.03% 3,3' diamino benzidine tetrahydrochloride, Fluka, Switzerland) and 0.2 mM imidazole (Sigma) in PBSA. After further washing in water for 5 minutes, sections were counterstained with Mayer's haematoxylin and blueing solution, before dehydration in absolute alcohol, clearing in xylol and mounting.

RESULTS

Cellular Reactivity of WM-65

The hybridoma selected, F56-1D5, secreted a murine IgG$_1$ Mab which was designated WM-65. Its reactivity with both normal and leukaemic haemopoietic cells is detailed in Tables 1 & 2. WM-65 reacted with over 90% of peripheral blood mononuclear cells (FIG. 1) and granulocytes, but not with normal platelets or erythrocytes (Table 1). It reacted with virtually all thymocytes and tonsil lymphocytes, as well as with the majority of normal bone marrow mononuclear cells. However, in myeloid progenitor assays, WM-65 reacted with only a minority (mean value 13.6%, range 2–34%, 5 experiments) of normal CFU$_{GM}$ (Table 3). The reactivity of WM-65 with PHA-stimulated T lymphoblasts was equivalent to that seen on resting normal T lymphocytes. Based on dye exclusion studies, WM-65 was incapable of lysing mononuclear cells in the presence of rabbit serum.

The reactivity of WM-65 with cell lines and leukaemic cells is also shown in Table 2. WM-65 reacted with all pre-B and B cell lines tested as well as 4/5 T cell lines, but with only ¼ myeloid cell lines. WM-65 showed extensive reactivity with leukaemic cells; including 8/8 cases of common acute lymphoblastic leukaemia (c-ALL), 4/4 B-chronic lymphatic leukaemia (B-CLL) and 2/2 hairy cell leukaemia (HCL), together with 13/13 acute myeloid

TABLE 1
REACTIVITY OF WM-65 WITH NORMAL HAEMOPOIETIC CELLS

| CELL TYPE | PERCENTAGE POSITIVE[a] | |
|---|---|---|
| Peripheral blood mononuclear cells | | |
| Total | 96.6 +/− 2.8 | (n = 7) |
| T lymphocytes (CD-3+) | 96.6 +/− 4.0 | (n = 4) |
| B lymphocytes (CD-20+) | 97.5 +/− 0.9 | (n = 4) |
| monocytes (CD-11c+) | 97.5 +/− 0.5 | (n = 4) |
| Granulocytes | 96.2 +/− 1.5 | (n = 5) |
| Platelets | 1 | (n = 5) |
| Erythrocytes | 1 | (n = 5) |
| Thymocytes | 91.5 +/− 0.5 | (n = 2) |
| Tonsil lymphocytes | 90.5 +/− 5.5 | (n = 2) |
| Bone marrow mononuclear cells | 63.2 +/− 10.6 | (n = 5) |

Footnotes
[a]Percentage of cells +/− 1 standard deviation positive above negative control by immunofluorescence.

TABLE 2
REACTIVITY OF WM-65 WITH LEUKAEMIC CELLS AND CELL LINES

| | CELL TYPE | PERCENTAGE POSITIVE |
|---|---|---|
| (A) | Leukaemias[a] | |
| | C-ALL | 8/8[b] |
| | T-ALL | 2/5 |
| | AML | 13/13 |
| | CML | 5/6 |
| | B-CLL | 4/4 |
| | T-CLL | 1/1 |
| | Hairy cell leukaemia | 2/2 |
| | PLL | 1/1 |
| (B) | Leukaemic cell lines | |
| | B cell | |
| | Daudi | 98[c] |
| | Raji | 98 |
| | Bristol 8 | 98 |
| | T cell | |
| | T-ALL-1 | 90 |
| | MOLT-4 | 98 |
| | RPMI-8402 | 1 |
| | CEM | 98 |
| | HSB-2 | 98 |
| | Pre-B | |
| | NALM-6 | 98 |
| | Reh | 72 |
| | KM-3 | 55 |
| | Myeloid | |
| | K-562 | 98 |
| | HL-60 | 5 |
| | RC-2A | 5 |
| | U937 | 5 |
| (C) | Non-haemopoietic tumor cell lines | |
| | Melanoma | 0/1 |
| | Squamous cell carcinoma | 0/2 |
| | Fallopian carcinoma | 0/1 |
| | Ovarian carcinoma | 0/4 |
| | Cervical carcinoma | 0/2 |
| | Neuroblastoma | 0/1 |

TABLE 2-continued

REACTIVITY OF WM-65 WITH
LEUKAEMIC CELLS AND CELL LINES

| CELL TYPE | PERCENTAGE POSITIVE |
|---|---|
| Breast carcinoma | 0/1 |

Footnotes
[a]Abbreviations used: C-ALL, common form of acute lymphoblastic leukaemia; T-ALL, T cell form of ALL; AML, acute myeloid leukaemia; CML, chronic myeloid leukaemia; B-CLL, B cell form of chronic lymphatic leukaemia; T-CLL, T cell form of CLL; PLL, prolymphocytic leukaemia.
[b]Number of cases considered to be positive with WM-65, with 20% of cells fluorescent above negative control, over total number tested.
[c]Percentage of cells fluorescent above negative control for each cell line.

TABLE 3

REACTIVITY OF WM-65 WITH NORMAL BONE
MARROW MYELOID PROGENITOR CELLS[a]

| FRACTION | NUMBER OF $CFU_{GM}$ | |
|---|---|---|
| | EXPERIMENT 1 | EXPERIMENT 2 |
| UNSEPARATED | 125 (100) | 266 (100) |
| WM-65+ | 9 (5) | 174 (34) |
| WM-65− | 164 (95) | 332 (66) |

Figure 1A:
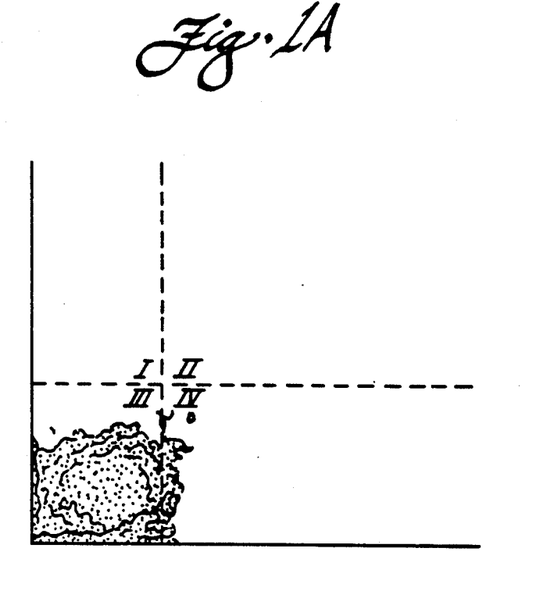
In FIG. 1A, cells were labelled with negative control Mabs directly conjugated with FITC or PE.
Figure 1B:
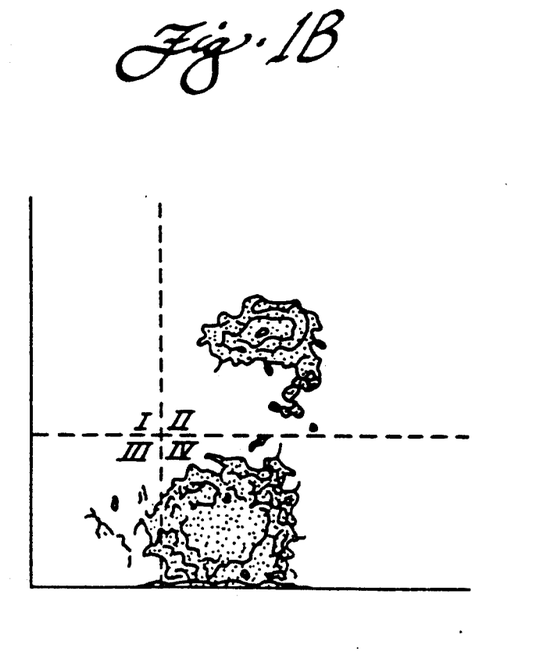
In FIGS. 1B, 1C and 1D cells were labelled with WM-65 directly conjugated with FITC, and CD-19 Mab (B4-PE.
Figure 1C:
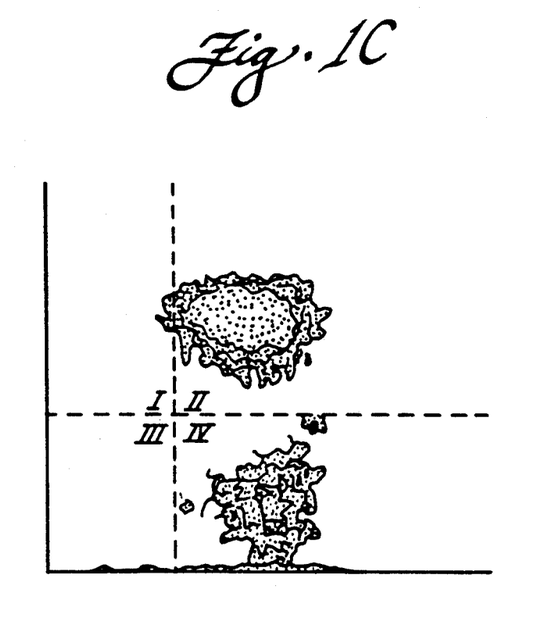
Figure 1D:
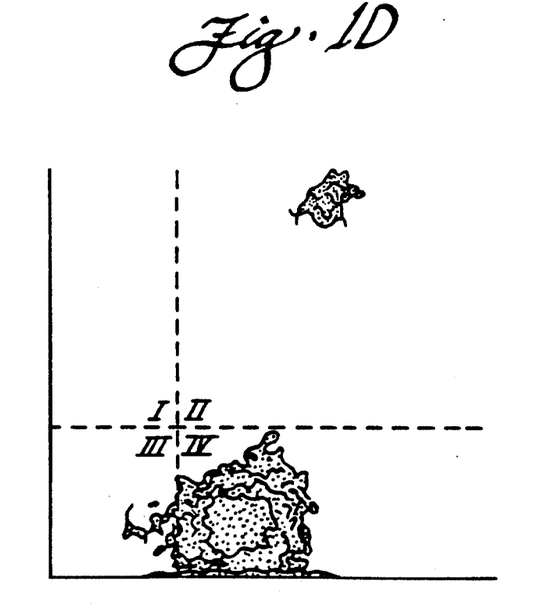
Figure 2A:
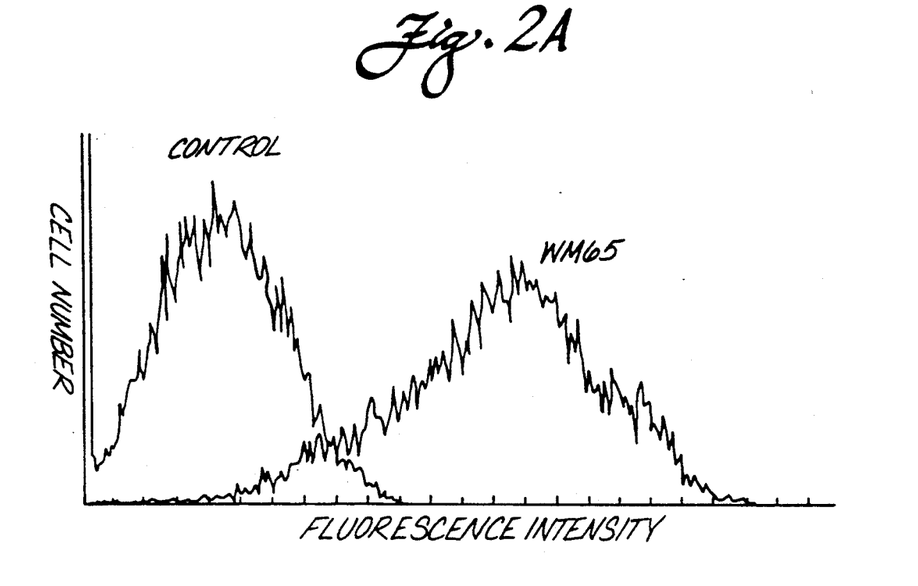
Figure 2B:
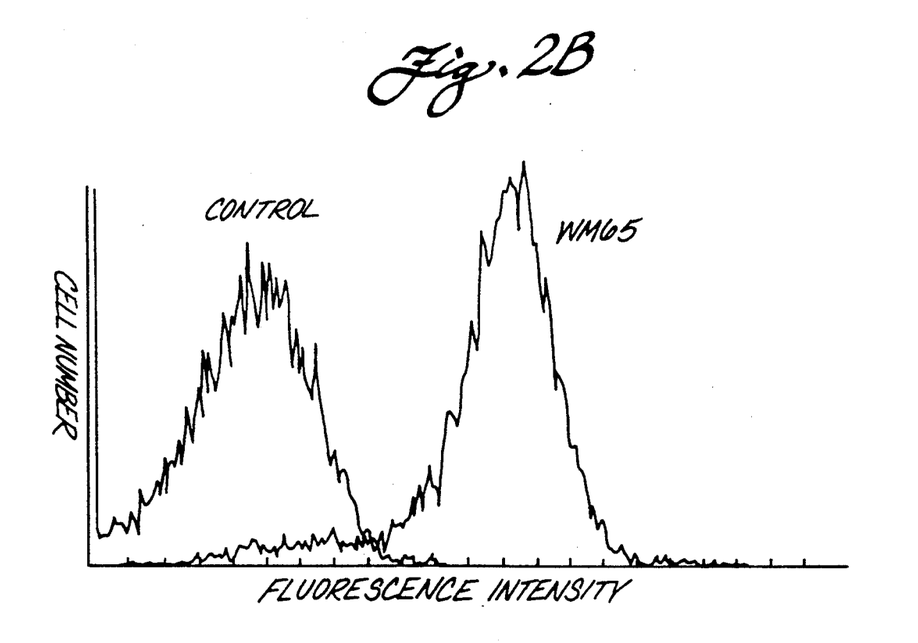

Footnote
[a]Bone marrow cells incubated with WM-65 and SAM-FITC, and passed through a FACS 440 cell sorter, either unsorted, or sorted into fluorescence-positive and negative populations. Two representative experiments are shown $CFU_{GM}$ values were adjusted to $10^5$ cells per plate, with assays being performed in quadruplicate, and mean values tabulated above. Values in parentheses indicate the proportion of $CFU_{GM}$ in each population. Proportion of bone marrow cells positive for WM-65 was 47% in Experiment 1, and 60% in Experiment 2.

leukaemia (AML) and 5/6 chronic myeloid leukaemia (CML) (FIG. 2). The percentage of cells positively stained by WM-65 in each case of acute leukaemia was generally high, with a mean of 71.7% of AML blasts (range 35.3–96.5) labelled, and mean 75.6% (range 21.8–90.7) ALL cells positive for WM-65. All non-haemopoietic cell lines tested were negative (Table 2).

Immunochemical Characterization of the Antigen Recognised by WM-65

Figure 3:
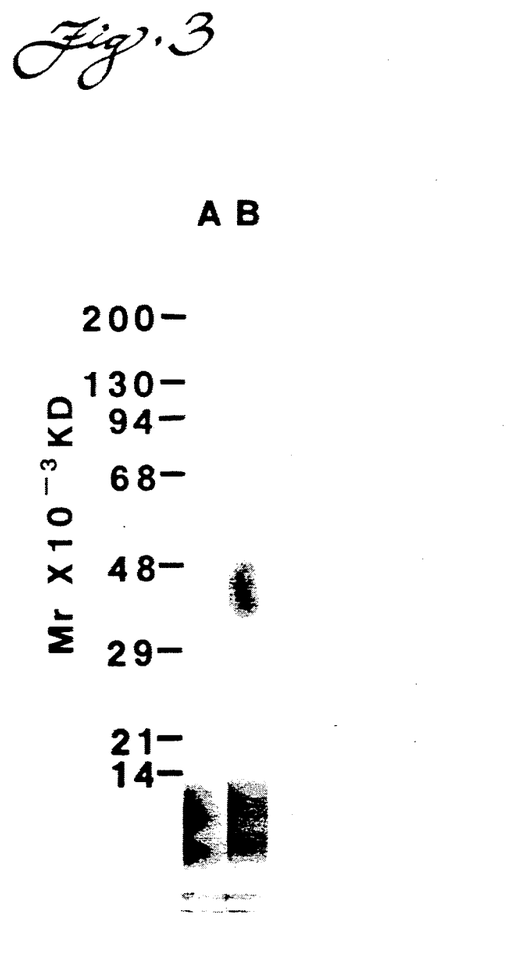
FIG. 3 shows the autoradiograph of immunoprecipitation and SDS-PAGE experiment on $^{125}I$-labelled leucocytes. Lane A, $IgG_1$ negative control Mab; Lane B, WM-65 immunoprecipitation. Position of molecular weight markers are indicated on the left. A broad band in the range of 40-50 Kilodaltons is seen in lane B.

SDS-polyacrylamide gel electrophoresis of $^{125}$I-surface-labelled peripheral blood mononuclear cells revealed that WM-65 immunoprecipitated a broad band with an apparent molecular weight between 40–50KD under both reduced and non-reduced conditions (FIG. 3).

Non-Haemopoietic Tissue Reactivity of WM-65

Frozen sections of normal tissues were evaluated for WM-65 reactivity by immunoperoxidase using an avidin-biotin-peroxidase complex. WM-65 was reactive with virtually all lymphoid cells and macrophages in both lymph node and tonsil, but showed no staining of salivary gland, lung, kidney, skeletal muscle and heart, apart from occasional lymphoid cells and macrophages.

WM-65 reacts with a novel human leucocyte differentiation antigen with wide distribution within the haemopoietic system. On immunoprecipitation and polyacrylamide gel electrophoresis, the antigen can be identified as a single broad band of molecular weight in the range of 40–50 Kilodaltons, indicating that it is likely to be a single polypeptide with heavy but variable glycosylation. This antigen is expressed on virtually all nucleated bone marrow-derived cells and lymphocytes, but was not detectable on non-haemopoietic cells.

It is interesting to note that although a high proportion of bone marrow mononuclear cells were reactive with WM-65, these did not include the majority of myeloid progenitors as judged by $CFU_{GM}$ assays, indicating that the antigen detected by WM-65 may be maturation linked, and expressed only as lymphocytes mature from earlier marrow stem cells. However, WM-65 did react with immature malignant haemopoietic cells, including leukaemic cell lines as well as cases of both ALL and AML.

Overall the data indicate that WM-65 reacts with an antigen not previously described. A number of leucocyte antigens with broad non-lineage specific distribution have been described previously (Pizzolo et al., 1980, Cancer, 46 2640–2647; Dalchau et al., 1980, European Journal of Immunology, 10, 737–744; Becker et al., 1981, Pathology, 13, 669–680; Hale et al., 1983, Blood, 62, 873–882; Vaughan et al., Transplantation, 36, 446–450). Differences in both molecular weight and cellular distribution distinguish these previously described antigens from the antigen recognised by WM-65 (Table 4). Class I MHC antigens have a molecular weight of 47KD, and are associated with the cell membrane of $B_2$-microglobulin (12KD) (Strominger, 1980, In Progress in Immunology Vol. 4, London Academic Press, p 539). Although the HLA heavy chain is closely similar to that of the WM-65 antigen, no molecular weight band comparable to the B-2M was seen on immunoprecipitation with WM-65. In addition, class I antigens are present on platelets but not on the B cell line Daudi, a pattern of expression opposite to that seen with WM-65 (Barnstable et al., 1978, Cell, 14, 9–20; Brown et al. 1979, European Journal of Immunology, 9, 272–275). The T200 or leucocyte common antigens (CD-45) have a molecular weight in the range of 180–220KD (Cobbold et al., 1987, In Leucocyte Typing III. White Cell Differentiation Antigens Oxford University Press, P788–803). Although the cellular reactivity patterns of CD-45 Mabs and WM-65 are very similar (Table 3), the molecular weights of the antigens recognised are

TABLE 4

COMPARISON OF WM-65 WITH OTHER NON-LINEAGE
SPECIFIC ANTIBODIES[a]

| CELL LINE | WM-65 | CD45 | CLASS II | PHM-1 | HuLyM3 | CAMPATH |
|---|---|---|---|---|---|---|
| PBL | +[b] | + | + | + | + | + |
| Granulocytes | + | + | + | + | + | +/− |
| Patelets | − | − | + | − | − | − |
| HSB-2 | + | + | + | + | + | +/− |
| U937 | − | + | + | + | + | − |
| KM3 | + | + | + | + | + | + |
| K562 | + | + | + | + | − | + |
| Reh | + | + | + | + | + | + |

TABLE 4-continued

COMPARISON OF WM-65 WITH OTHER NON-LINEAGE SPECIFIC ANTIBODIES[a]

| CELL LINE | WM-65 | CD45 | CLASS II | PHM-1 | HuLyM3 | CAMPATH |
|---|---|---|---|---|---|---|
| MW (K.D)[c] | 40-50 | 220-180 | 47,12 | 180,62 | 47 | 23-30 |

Footnotes
[a]All cellular reactivities determined in the inventors' laboratory.
[b]+: reactivity 20%, +/−: reactivity 15-20%,
−: reactivity 15% by indirect immunofluorescence and flow cytometry.
[c]Antigen molecular weights quoted from original references.

clearly different.

Three other Mabs with similar reactivity have been described. PHM$_1$ reacts with lymphocytes, granulocytes and several cell lines, and immunoprecipitates an antigen of molecular weight 180/62KD (Becker et al., 1981, Pathology, 13, 669-680). Aside from this report of molecular weight, the major property distinguishing PHM-1 from WM.65 is that the former reacts with the U937 cell line, which is unreactive with WM-65. The pan leucocyte Mab HuLyM3 immunoprecipitates an antigen of 47KD molecular weight, with a cellular distribution closely similar to that of WM-65 (Vaughan et al., Transplantation, 36, 446-450). However, HuLyM3 does not react with the myeloid cell line K562, which is moderately strongly labelled by WM.65, indicating that the two Mabs identify different antigens. Finally, CAMPATH-1 can be distinguished from all the above in that it does not react with granulocytes to any significant degree, and precipitates a broadly glycoslated band of 23-30 KD (Hale et al., 1983, Blood, 62, 873-882; Cobbald et al., 1987, In Leucocyte Typing III. White Cell Differentiation Antigens. Oxford University Press, P788-803).

The above data indicates that the 40-50 Kilodalton molecule identified by WM-65 Mab is a newly recognised leucocyte surface membrane antigen. Although its restricted distribution to the haemopoietic family of cells suggests some functional significance, no physiological role for the molecule has yet been investigated. The major practical feature of interest with this Mab is its extensive reactivity with acute and chronic leukaemias of both myeloid and lymphoid types. This is an unusual property for a monoclonal antibody, and raises the interesting possibility that the antibody may be useful in the treatment of haematological malignancies. This is heightened by the fact that WM-65 has comparatively little reactivity with bone marrow progenitor cells, and might therefore allow therapy to be selectively targeted to malignant haemopoietic cells. Although the antibody is not complement-fixing, it may have clinical application if it was conjugated to a toxin, drug or radioisotope. Preliminary studies to link the biological toxin ricin to WM-65 are underway to explore this possibility.

We claim:

1. A mouse monoclonal antibody produced by the hydridoma cell line designated F56-1D5 (ECACC 89033001).

2. A hybridoma cell line in which the cell line is designated F56-1D5 (ECACC 89033001).

UNITED STATES PATENT AND TRADEMARK OFFICE
CERTIFICATE OF CORRECTION

PATENT NO.  : 5,179,019         Page 1 of 2

DATED       : January 12, 1993

INVENTOR(S) : Kenneth F. Bradstock; Michael K. Atkinson; Anthony J. Henniker

It is certified that error appears in the above-identified patent and that said Letters Patent is hereby corrected as shown below:

Column 1, line 9, after "line" insert a period.
Column 1, line 18, change "product" to -- produce --.

Column 2, line 4, change "HSBO2" to -- HSB-2 --.

Column 3, line 22, change "autoradiagraph" to -- autoradiograph --.
Column 3, line 27, change "Kilodaltons" to -- kilodaltons --.
Column 3, line 37, after "injected" insert a period.
Column 3, line 55, after "method" insert a period.

Column 5, line 3, after "method" insert a period.
Column 5, line 4, change "detergents" to -- detergent, --.
Column 5, line 5, after "material" insert a period.
Column 5, lines 8,9, change "minutes" to -- minute --.
Column 5, line 10, change "PABNSORBIN" to -- PANSORBIN --.
Column 5, line 12, after "mercaptoethanol" insert a period.
Column 5, line 23, after "nitrogen" insert a period.

UNITED STATES PATENT AND TRADEMARK OFFICE
CERTIFICATE OF CORRECTION

PATENT NO. : 5,179,019

DATED : January 12, 1993

INVENTOR(S) : Kenneth F. Bradstock; Michael K. Atkinson
Anthony J. Henniker

It is certified that error appears in the above-identified patent and that said Letters Patent is hereby corrected as shown below:

In the Claims

Column 10, line 32, change "hydridoma" to -- hybridoma --.

Signed and Sealed this

First Day of March, 1994

Attest:

BRUCE LEHMAN

Attesting Officer   Commissioner of Patents and Trademarks